United States Patent
Grohowski, Jr.

(10) Patent No.: US 9,089,431 B2
(45) Date of Patent: Jul. 28, 2015

(54) CONTROLLED POROSITY ARTICLE

(71) Applicant: Praxis Powder Technology, Inc., Queensbury, NY (US)

(72) Inventor: Joseph A. Grohowski, Jr., Glens Falls, NY (US)

(73) Assignee: Praxis Powder Technology, Inc., Queensbury, NY (US)

( * ) Notice: Subject to any disclaimer, the term of this patent is extended or adjusted under 35 U.S.C. 154(b) by 208 days.

(21) Appl. No.: 13/930,803

(22) Filed: Jun. 28, 2013

(65) Prior Publication Data

US 2013/0289735 A1    Oct. 31, 2013

Related U.S. Application Data

(60) Division of application No. 11/450,059, filed on Jun. 9, 2006, now Pat. No. 8,500,843, which is a continuation-in-part of application No. 10/884,444, filed on Jul. 2, 2004, now Pat. No. 7,674,426.

(51) Int. Cl.
*A61F 2/34* (2006.01)
*A61F 2/30* (2006.01)
(Continued)

(52) U.S. Cl.
CPC .............. *A61F 2/34* (2013.01); *A61F 2/30767* (2013.01); *A61F 2/30771* (2013.01); *A61L 27/04* (2013.01); *A61L 27/56* (2013.01); *B01D 39/2093* (2013.01); *B22F 3/1109* (2013.01); *B22F 3/1121* (2013.01); *B22F 3/1134* (2013.01); *B29C 43/006* (2013.01); *A61F 2/3094* (2013.01); *A61F 2/32* (2013.01); *A61F 2/36* (2013.01); *A61F 2/3662* (2013.01); *A61F 2002/30011* (2013.01); *A61F 2002/30929* (2013.01); *A61F 2002/30957* (2013.01); *A61F 2002/30968* (2013.01); *A61F 2250/0023* (2013.01); *A61F 2310/00017* (2013.01); *A61F 2310/00023* (2013.01); *A61F 2310/00029* (2013.01);

(Continued)

(58) Field of Classification Search
CPC ........ A61F 2/34; B22F 3/114; B01D 39/2093
USPC ....................................... 623/22.21
See application file for complete search history.

(56) References Cited

U.S. PATENT DOCUMENTS 2,672,415 A    3/1954    Balke
3,138,857 A    6/1964    Kuchek
(Continued)

FOREIGN PATENT DOCUMENTS

WO    2001019556 A1    3/2001
WO    2004039748 A1    5/2004

OTHER PUBLICATIONS

Extended European Search Report received for EP Patent Application No. 05763915.5, mailed on Jun. 14, 2010, 9 pages.
(Continued)

*Primary Examiner* — Weiping Zhu
(74) *Attorney, Agent, or Firm* — Lerner, David, Littenberg, Krumholz & Mentlik, LLP

(57) ABSTRACT

In one embodiment, the present invention is a porous article including a porous portion with an average ratio between about 2:1 and about 5:1 of major pore size to minor pore size, having a substantially uniform pore distribution and a porosity of at least 70 percent, the porous article for use as a biological implant. The biological implant can be, for example, an acetabular cup.

3 Claims, 7 Drawing Sheets

(51) Int. Cl.
- *A61L 27/04* (2006.01)
- *A61L 27/56* (2006.01)
- *B01D 39/20* (2006.01)
- *B22F 3/11* (2006.01)
- *B29C 43/00* (2006.01)
- *A61F 2/32* (2006.01)
- *A61F 2/36* (2006.01)
- *B29L 31/00* (2006.01)

(52) U.S. Cl.
CPC ............... *A61F2310/00047* (2013.01); *A61F 2310/00071* (2013.01); *A61F 2310/00077* (2013.01); *A61F 2310/00095* (2013.01); *A61F 2310/00131* (2013.01); *B22F 2998/00* (2013.01); *B22F 2998/10* (2013.01); *B29L 2031/7532* (2013.01)

(56) References Cited

U.S. PATENT DOCUMENTS

| | | | |
|---|---|---|---|
| 3,362,818 | A | 1/1968 | Schwarzkopf et al. |
| 3,802,878 | A | 4/1974 | Lindstrom |
| 3,852,045 | A | 12/1974 | Wheeler et al. |
| 4,588,540 | A | 5/1986 | Kiefer et al. |
| 6,008,281 | A | 12/1999 | Yang et al. |
| 6,022,509 | A | 2/2000 | Matthews et al. |
| 6,174,493 | B1 | 1/2001 | Asbury |
| 6,582,470 | B1 | 6/2003 | Lee et al. |
| 6,592,787 | B2 | 7/2003 | Pickrell et al. |
| 6,846,862 | B2 | 1/2005 | Schofalvi et al. |
| 7,674,426 | B2 | 3/2010 | Grohowski, Jr. |
| 2002/0086039 | A1 | 7/2002 | Lee et al. |
| 2002/0151985 | A1 | 10/2002 | Kuberasampath et al. |
| 2002/0153348 | A1 | 10/2002 | Say et al. |
| 2003/0044301 | A1 | 3/2003 | Lefebvre et al. |
| 2003/0153981 | A1 | 8/2003 | Wang et al. |
| 2004/0072010 | A1 | 4/2004 | Date et al. |
| 2006/0003179 | A1 | 1/2006 | Wang et al. |
| 2006/0228247 | A1 | 10/2006 | Grohowski |
| 2010/0094420 | A1 | 4/2010 | Grohowski, Jr. |

OTHER PUBLICATIONS

Hens, K. F. "Thermat expands precision PIM operation", Elsevier Science Ltd., 1998, 3 pages.
International Search Report and Written Opinion for PCT/US2005/23118 dated Oct. 24, 2005.
International Search Report and Written Opinion for PCT/US2007/13416 dated Nov. 21, 2007.
Laptev et al., "Study of production route for titanium parts combining very high porosity and complex shape", Powder Metallurgy, vol. 47, No. 1, 2004, pp. 85-92.

CONTROLLED POROSITY ARTICLE

CROSS-REFERENCE TO RELATED APPLICATIONS

The present application is a divisional of U.S. application Ser. No. 11/450,059, filed on Jun. 9, 2006, which is a continuation-in-part of U.S. application Ser. No. 10/884,444, filed on Jul. 2, 2004, the disclosures of which are hereby incorporated herein by reference.

BACKGROUND

Embodiments described relate to porous articles formed having a controlled level of porosity that may be substantially evenly distributed throughout portions thereof. Embodiments described herein relate to the forming of a porous metal by way of techniques that minimize health hazards as well as hazards to the character of the porous metal itself.

BACKGROUND OF THE RELATED ART

Porous metal articles are used in many applications including orthopedic implants, bone growth media, filters, sound suppression materials, fuel cells, catalyst supports, and magnetic shielding. Such porous articles may have open or closed porosity as well as a wide range of pore size, shape, density, and distribution. The specific structures and properties required depend on the application.

In order to provide a degree of control over the porosity exhibited by the metal article, a solid pore former may be utilized when making the metal article. For example, a metal vapor or powder form of a metal may be deposited a solid foam matrix to accommodate pore forming. Alternatively, the metal may be mixed with a pore former consisting of polymer or other suitable material beads. In either case, the pore former is of a stable predetermined size, shape and other physical characteristics. Thus, once the metal is hardened, removal of the solid pore former leaves behind an article that displays a largely predetermined and controlled pore size and shape.

Employing a solid pore former as noted above provides a degree of control over the resulting pore size and shape within the porous metal article as compared to techniques which fail to make use of such a pore former. For example, in an alternative foaming technique porosity is ultimately determined by the fairly chaotic nature of a dissolved gas dispersing through a liquefied metal. In another alternative diffusion bonding or sintering technique, porosity is determined by and limited to the naturally present space between metal powder or granules filling a mold tool. In either case, the lack of a solid pore former leaves much of the process of pore formation to chance.

In exercising a greater degree of control over porosity, techniques of employing solid pore formers vary. For example, as noted above, a solid foam matrix may be employed as a pore former. This technique may include deposition of a metal onto the solid foam matrix. This may be accomplished by dipping the foam matrix in a slurry containing the metal in powder form. Alternatively, vapor deposition techniques may be employed to provide a metal coating to the solid foam matrix. Regardless, subsequent evaporation and condensation of the material on the substrate may follow to provide a porous metal article. Thereafter, the article may harden and the foam material may be removed through various techniques, such as vaporization.

As also noted above, pore formers may be utilized in the form of pore forming beads mixed with a fluid or powdered metal. Once mixed, the metal may be hardened through a variety of techniques, such as sintering. Subsequent removal of the pore forming beads leaves behind a porous metal structure.

While providing a degree of control to pore formation, there unfortunately remain significant inherent limitations to techniques employing solid pore formers. For example, in the case of a solid foam matrix, the ability of a metal vapor or powder to penetrate and evenly coat the matrix substrate is subject to inherent limitations relative to metal particle and matrix pore sizes. That is, with a thick enough matrix, the natural accumulation of metal clogged matrix pores will prevent deposition of the metal from proceeding further into the matrix. Thus, larger and thicker porous metal articles may not practically be formed by use of a foam matrix technique. In the case of pore forming beads mixed with a fluid or powdered metal, the beads tend to be present in somewhat of a free floating nature within the metal. As such, the beads have a tendency to settle and fail to remain evenly distributed throughout the mixture. As a result, the porous metal article which is formed can end up with pores that are not evenly distributed throughout.

Further, regardless of the type of solid pore former employed, its removal following formation of the article often subjects it to vaporization or other stressors likely to affect the physical character of the porous metal article. This can deter the use of the porous metal article as an option for sensitive applications such as for use as a biological implant.

At present, selection of a technique employing a solid pore former either limits the thickness of the porous metal article to be formed or increases the likelihood of an uneven pore distribution throughout the porous metal article. Further, in either case, removal of the pore former can affect the resulting physical character of the porous metal article.

SUMMARY OF THE INVENTION

An article of controlled porosity is provided. The porosity is controlled by a coated pore former that includes pore former and homogenizing agent. The coated pore former is mixed with a material such as a metal whereby the homogenizing agent maintains a uniform distribution of pore former through the metal.

DETAILED DESCRIPTION

Embodiments are described with reference to certain porous metal articles of tailored porosity. These may include metal articles in the form of biological implants having a final porosity that is uniformly distributed and exceeds 50-80% by volume of the article. However, embodiments described herein may be applicable to a host of porous articles for a variety of uses. For example, metal filters and other articles described further herein may be formed by the techniques described below. Additionally, the porous articles may be of ceramic based or other non-metal material. Additionally, articles exhibiting any degree of porosity may similarly be formed by the techniques described. Furthermore, the tailored porosity may be in the form of a controlled uniform pore distribution or by way of multiple metal layers varying porosity provided within a single article. Regardless, embodiments described herein allow the porosity provided within a metal article to be both tightly controlled and tailored throughout.

Figure 1:
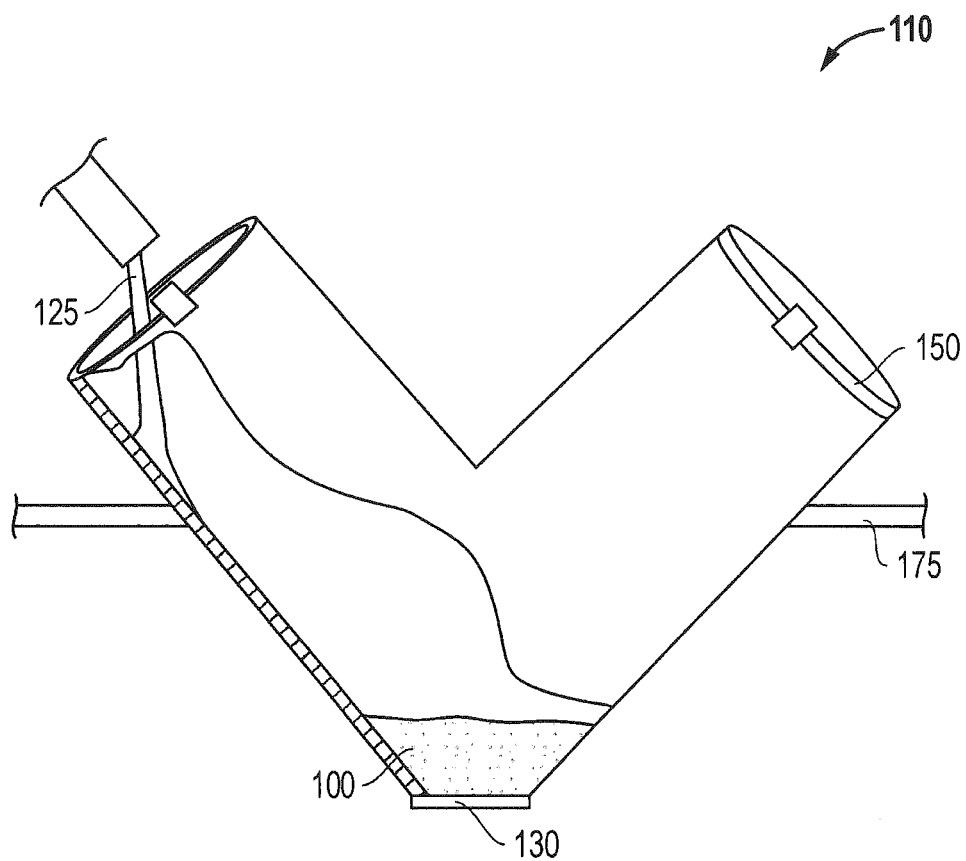
FIG. 1 is a perspective sectional view of a blender containing an embodiment of a coated pore former for combining with a metal.

Referring to FIG. 1, an embodiment of a coated pore former 100 is shown contained within a conventional v-blender 110. With additional reference to FIG. 2, the coated pore former 100 is a pore former 250 present as particles coated with a homogenizing agent 255 as described further herein. In the embodiment shown, metal 125 in powder form is mixed with the coated pore former 100 to provide a pore forming metal mixture 200 of pore formable metal. However, in other embodiments a ceramic, such as zirconia powder may be used to form a non-metal porous article. Continuing with the embodiment shown, the homogenizing agent 255 allows the coated pore former 100 to remain substantially evenly distributed throughout the mixture 200 without settling. As also described further herein, the coated pore former 100 is an extractible particulate that acts to physically define porosity once it has been removed. As a result, a porous metal article 600 or portion thereof may be formed from the mixture 200 that displays pores evenly distributed throughout (see FIG. 6).

Figure 2:
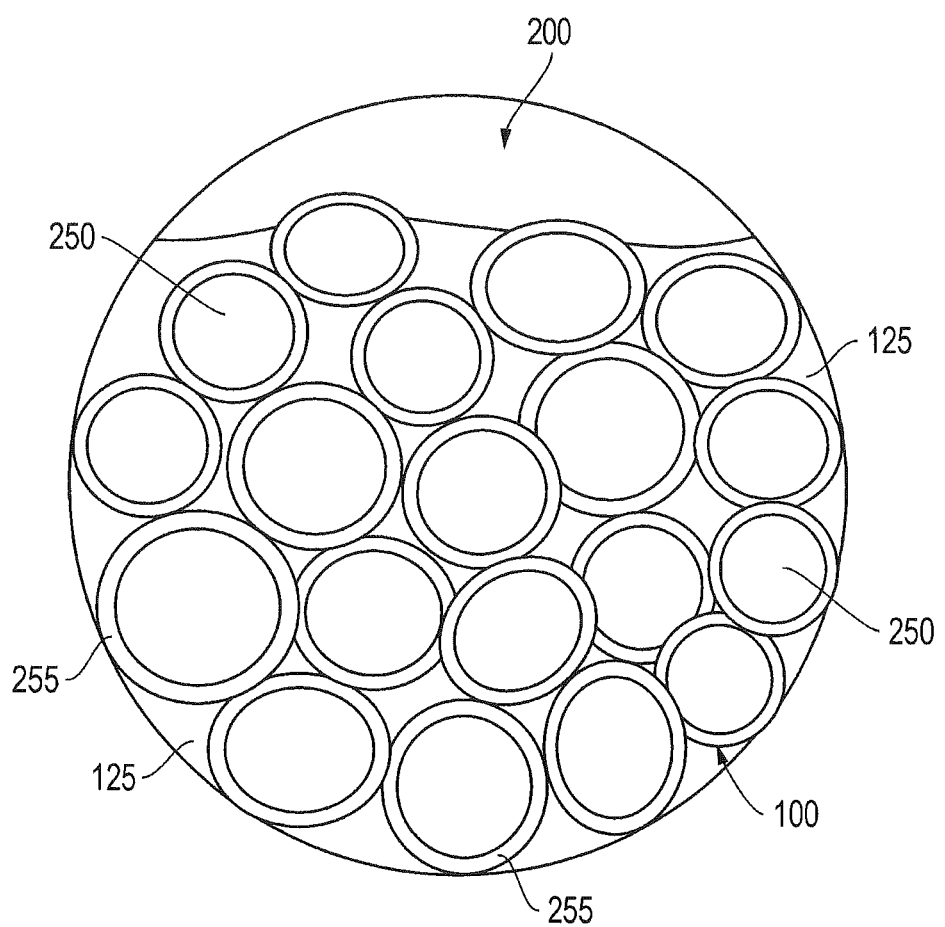
FIG. 2 is an enlarged view of an embodiment of a mixture of the coated pore former and metal of FIG. 1.
Figure 6:
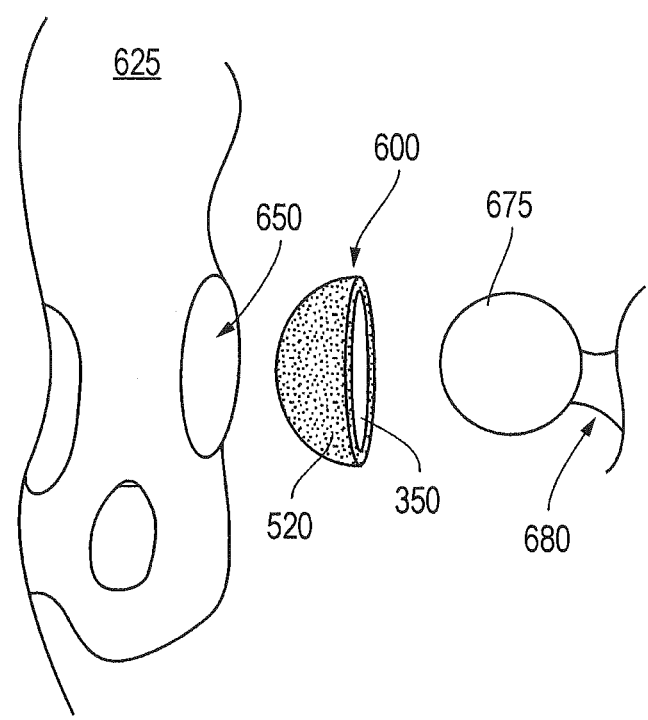
FIG. 6 is an exploded perspective view of an embodiment of a porous metal article formed from the green article of FIG. 5 and of tailored porosity for use as a biological implant.

Continuing with reference to FIGS. 1, 2, and the porous metal article 600 of FIG. 6, the coated pore former 100 may include a pore former 250 coated by a homogenizing agent 255 as noted above. The pore former 250 itself may be selected based on morphology with the size and shape of pores in the porous metal article 600 in mind. For example, pore formers 250 may appear granular, bead-like, spherical, irregular or angular depending on the pore morphology type desired in the porous metal article 600. In terms of size, embodiments of pore formers 250 described herein may range roughly from about 50 to about 2,000 microns in diameter. However, a variety of other pore former 250 sizing may be employed. Once more, a range of particle size and shape distribution of the pore former 250 may be employed within a given mixture 200. For example, a host of milling, grinding, sieving, and air classification techniques may be employed to provide a particular particle size and/or morphology distribution configured. These particle characteristics may be provided with the size and shape of the pores to be provided to the porous metal article 600 in mind.

The selection of the constituents of the mixture 200 may take into account the processing conditions to be encountered. For example, a pore former 250 may be selected that is mechanically capable of withstanding compaction in order to maintain definition of a desired pore size and shape in the resulting porous metal article 600. As described further herein, embodiments of compaction may include the introduction of pressures in the range of about 25 to about 50 ksi (thousand pounds per square inch). Thus, the material of the pore former 250 may be selected in light thereof. Similarly, a material may be selected for the pore former 250 that it is compatible with fluid extraction for its removal from the mixture 200. Furthermore, given that sintering at elevated temperatures may follow extraction, pore formers 250 may be employed that are relatively larger than the pore size to be displayed in the final porous metal article 600. That is, as described further herein, sintering will likely result in some shrinkage of the metal 125 thereby reducing pore size following extraction of the pore formers 250. Therefore, the pore formers 250 may be accordingly oversized relative to the intended pore size found in the porous metal article 600.

With the above considerations in mind a variety of material types may be selected for the pore former 250. In particular, embodiments of pore formers 250 may include a host of naturally ionic materials such as metal salts. Metal salts such as potassium chloride, sodium chloride and mixtures thereof are particularly good candidates for removal through conventional water-based extraction techniques as described further herein. Additionally, metal salts are able to withstand conventional compaction techniques withstanding pressures of between about 25 and about 50 ksi without any significant deformation. In one embodiment, the pore former 250 is provided in the form of an oversized potassium chloride salt. In still other embodiments potassium sorbate or sugar may be employed as the pore former 250.

Continuing with reference to FIGS. 1 and 2, the pore former 250 is added to the v-blender 110 followed by the homogenizing agent 255. The homogenizing agent 255 may be added to the v-blender 110 through a conduit in its horizontal physical axis 175. This addition may take place over about a 5 to 10 minute period while mixing proceeds within the v-blender 110. The homogenizing agent 255 is provided in this manner to coat the pore formers 250 as shown in FIG. 2. As such the pore formers 250 are provided with characteristics that promote their even distribution throughout the mixture 200 once the metal 125 is provided as described below.

The homogenizing agent 255 may be a variety of materials selected to compatibly coat the pore former 250 while also displaying a physical reaction to the selected metal 125 of the mixture 200. For example, in one embodiment, a water soluble material such as polyethylene glycol (PEG) is used as the homogenizing agent 255 to coat the pore former 250 where it is to be mixed with a metal 125 such as titanium, as described further herein. In this embodiment, the PEG provides an actively disengaging character to the surface of the pore former 250 relative to the metal 125. Thus, the coated pore former 100 remains floating, relatively evenly distributed throughout the mixture 200. Stated another way, the metal 125 too remains substantially uniformly distributed relative to the pore former 250, rather than allowing the pore former 250 to settle. Alternative homogenizing agents which may be employed in this manner include alcohols, isoparafinic solvents, and organic liquids such as acetone.

In an alternate embodiment, a homogenizing agent 255 may be provided to coat the pore former 250 which provides an engaging character to the surface thereof with respect to a given metal 125. That is, in this embodiment, the physical reaction to the selected metal 125 is an attractive one. In this instance, each coated pore former 100 tends to adhere metal 125 thereto upon its introduction. Thus, coated pore formers 100 in this embodiment remain disbursed throughout the mixture 200 in a manner that promotes closed cell porosity upon pore former 250 removal, as described in greater detail below.

Continuing with reference to FIGS. 1 and 2, the coated pore former 100 is provided by mixing the pore former 250 with the homogenizing agent 255 in the v-blender 110 as indicated. In one embodiment, the pore former 250 may constitute between about 70-80% of the mixture 200 as a whole, with homogenizing agent 255 making up between about 5 and 10% of the mixture 200. These initial components of the coated pore former 100 may be mixed by conventional gentle mixing with the v-blender 110 for between about 10 and about 20 minutes or until the pore formers 250 are substantially coated with the homogenizing agent 255. This is accomplished by adding the pore formers 250 and homogenizing agent 255 to the v-blender 110 through either of the upper doors 150. Conventional v-mixing then proceeds with the v-blender 110 rotating about its horizontal physical axis 175.

Providing only up to the optimum amount of homogenizing agent 255 may allow more complete compression or compaction of the mixture 200 as described further herein. Therefore, while homogenizing agent 255 provides a controlled pore character, in terms of pore distribution, use of only up to an amount for coating the pore formers 250 is furthered by mixing of the pore formers 250 and homogenizing agent 255 thoroughly before addition of the metal 125 as described.

With added reference to FIG. 6, a final porous metal article 600 may experience a certain degree of shrinkage and other changes via processing techniques described below. Nevertheless, the ratio of constituents provided to the mixture 200 as described above may be configured with this in mind to provide a porosity of between about 60% and about 85% or greater to an overlay metal 520 (see FIG. 5). Furthermore, pores ranging in size from about 50 to about 2000 micrometers may ultimately be provided to the porous metal article 600 by way of techniques also described herein.

Once the coated pore former 100 is sufficiently mixed, metal 125 may then be added to the v-blender 110 as shown in FIG. 1. With additional reference to the porous metal article 600 of FIG. 6, the metal 125 may be provided in the form of a powder selected in light of subsequent processing as well as the intended use of the porous metal article 600. For example, where the mixture 200 is to undergo compaction for solidification, powdered metal 125 of an irregular, angular, or ligamental grade or nature may be employed to provide a higher tensile or green strength following compaction. Additionally, in order to promote complete and even compaction of the metal 125 and improve green strength, as described further herein, the metal 125 may be provided in the form of a metal powder having between about 1% and about 10% weight thereof in the form of a thermally decomposable conventional binder or lubricant additive.

A variety of types of metal 125 may be used to form the porous metal article 600. For example, in an embodiment where the porous metal article 600 is to be used as a biological implant, the metal 125 may be titanium, or other recognized biocompatible material. In addition to titanium, other types of metal 125 which may be employed include tantalum, cobalt chrome, niobium, stainless steel, nickel, copper, aluminum, and alloys thereof. In another embodiment the metal 125 is replaced with a ceramic powder such as zirconia to form a non-metal porous article akin to the techniques described below.

In the embodiment shown, the above selected metal 125 or other base material may constitute between about 15 and about 20% of the mixture 200 as a whole. Once added to the v-blender 110, mixing of the coated pore former 100 and the metal 125 may proceed by conventional means as described above. For example, in one embodiment, gentle mixing with the v-blender 110 may take place for up to about 10 minutes or until a substantially homogeneous mixture 200 of coated pore former 100 and metal 125 is achieved. Once this homogeneous mixture 200 is achieved, settling or separation of the coated pore former 100 is substantially avoided due to the presence of the homogenizing agent 255. Thus, processing of the mixture 200 may proceed without significant concern over maintaining an even distribution of pores throughout the porous metal article 600 (see FIG. 6). The homogenizing agent 255 stabilizes the mixture 200 allowing a more reliable distribution and precise tailoring of porosity.

Referring now to FIGS. 3-7 an embodiment of processing the homogeneous mixture 200 into a porous metal article 600 that is to be employed as a biological implant is described. However, embodiments of such a homogeneous mixture 200 may be processed into a variety of other types of articles for which a controlled or tailored porous metal structure would be of benefit. Such articles may include acoustical dampeners, flow control devices, metal filters, fluid applicators, catalytic support structures, friction material substrates, and a host of other devices.

Figure 3:
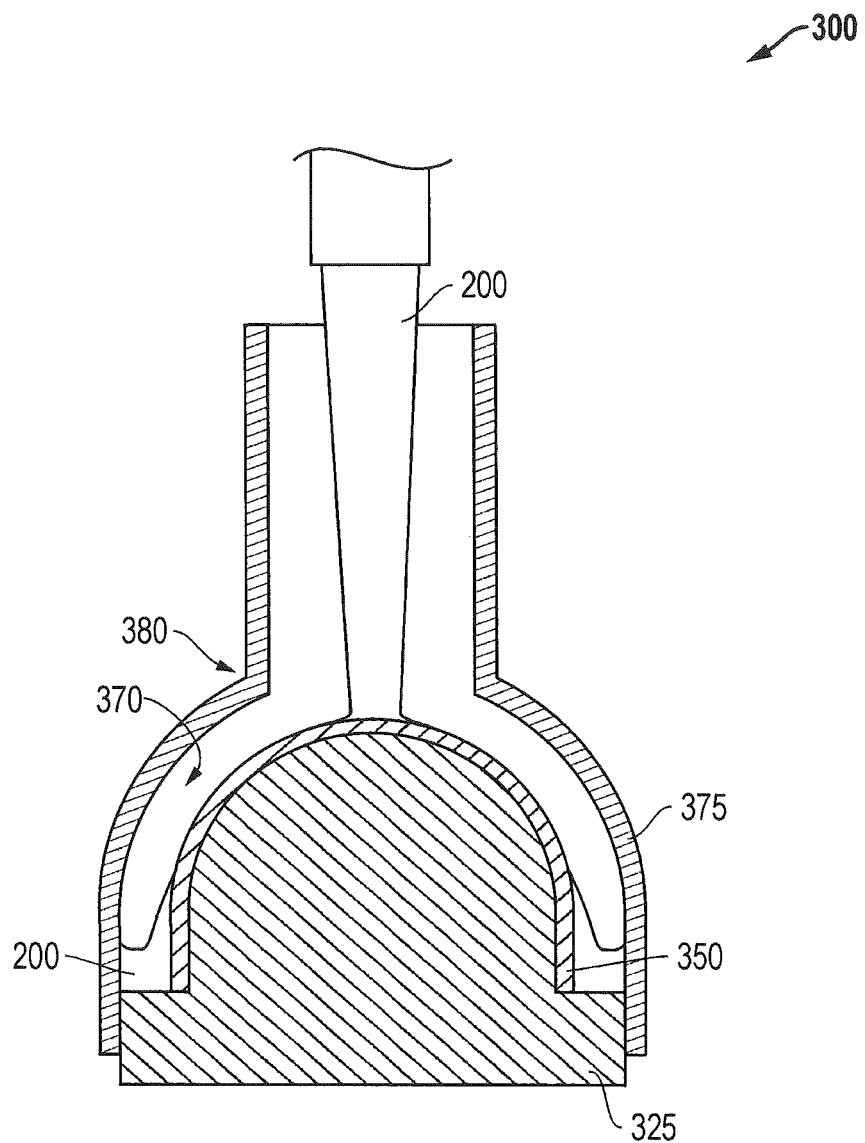
FIG. 3 is a side cross sectional view of an embodiment of a mold tool receiving the mixture of FIG. 2.

With particular reference to FIGS. 1, and 3-6 the mixture 200 is transported by conventional means from the lower door 130 of the v-blender 110 and to a mold tool 300 for consolidation or compaction. As shown, the mold tool 300 is enclosed at its lower portion by a mandrel 325 and a underlying metal 350. In the embodiment shown the underlying metal 350 is a compact of the same type of metal 125 as is present in the mixture 200. As shown in FIG. 3, the underlying metal 350 is in a green state and configured to display porosity that differs from the porosity to be provided by the mixture 200. As shown in FIG. 3, the mixture 200 is poured into the mold tool 300 over the mandrel 325 and underlying metal 350. Following compaction and other processing, the metal within the mixture 200 will make up the structure of an overlay metal 520 of the porous metal article 600.

Continuing with reference to FIGS. 3-6, the mandrel 325 is employed to provide a concave shape to the mixture 200 and/or the underlying metal 350 immediately thereabove. However, the mandrel 325 may be of a variety of shaping and support types depending upon the type of porous metal article 600 that is to be formed. In fact, the mold tool 300 may even be configured to provide a large block or cylinder shaped ingot for later shaping into an article of a desired final shape. In the particular embodiment shown, the mandrel 325 is provided for support of the mixture 200 and the underlying metal 350 thereabove during compaction as described below. Therefore, the mandrel 325 is preferably of a material differing from that of the layers of mixture 200 and underlying metal 350. In this manner, adherence of the layers to the mandrel 325 as a result of the compaction process may be avoided. For example, in one embodiment, the mixture 200 and the underlying metal 350 include metal in the form of titanium, whereas the mandrel 325 is of a solid stainless steel.

The embodiments shown in FIGS. 3-6 include the above-noted underlying metal 350. However, in alternative embodiments, any number of layers of underlying metal 350 may be provided (including none at all). In embodiments employing several such layers, each may be configured to display its own unique pore character in the final porous metal article 600. That is, each layer of underlying metal 350 may be independently formed to provide its own pore size, shape and distribution therethrough. Each layer of underlying metal 350 may be formed from its own metal-based mixture, each mixture to provide its own individual pore character. Further, each mixture may be followed by its own separate compaction to a green state as described here with the mixture 200 and overlay metal 520 shown. In this manner, multiple layers of varying porosity may ultimately be provided to a single porous metal article 600 as described further below.

In the embodiments shown, the underlying metal 350 is formed from a mixture that is a titanium powder without any pore forming components and is thus configured to display negligible if any porosity in the final porous metal article 600. Thus, as described further herein, an overlay metal 520 to display porosity and a underlying metal 350 to display no porosity are co-formed into the single porous metal article 600 (i.e. displaying a tailored porosity therethrough).

Figure 4:
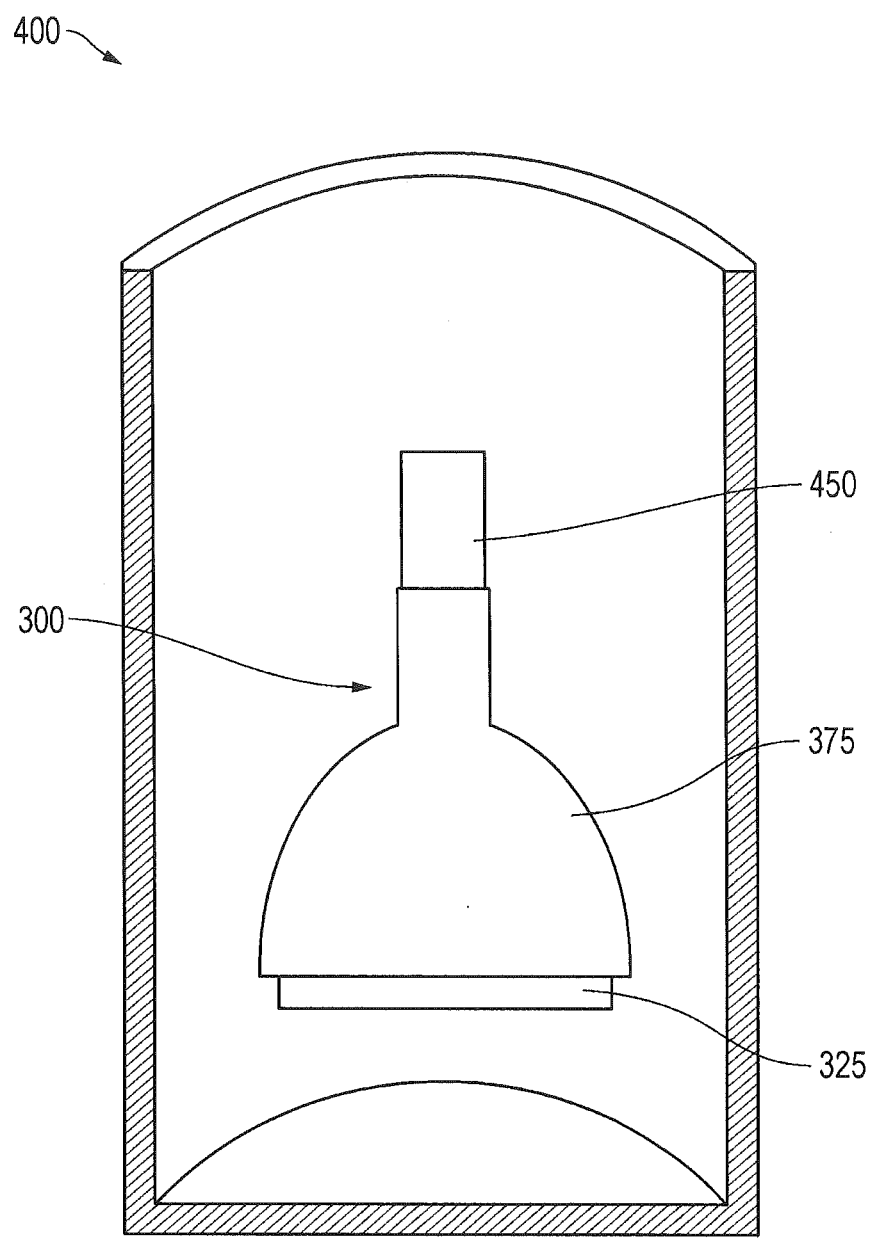
FIG. 4 is a side cross sectional view of an embodiment of a cold isostatic press chamber containing the mold tool of FIG. 3.

With particular reference to FIGS. 3 and 4, the mixture 200 is poured into the mold tool 300 taking up the space 370 between the underlying metal 350, mandrel 325, and the walls 375 of the mold tool 300 itself. This space 370 is filled until the mixture 200 reaches about the neckline 380 of the mold tool 300.

Once the mold tool 300 is filled, the mixture 200 may be dried for removal of the homogenizing agent 255 (see FIG. 2). For example, in one embodiment, drying may take place at between about 25° C. and about 75° C. for between about five minutes, and about one hour depending on the volume of the poured mixture 200, its exposure to outside air, and other factors. Alternatively, removal of the homogenizing agent 255 may be bypassed until later processing as described below.

The mold tool 300 is sealed with a plug 450 and may be rotated or tumbled several times to help eliminate any potential stratification of the mixture 200 within the mold tool 300. Additionally, the mold tool 300 may be tapped several times to assure proper filling. For example, in one embodiment, the mold tool 300 is forcibly impacted 20 to 60 times onto a table. The repeated landing of the mold tool 300 on the table helps to ensure that the mold tool 300 is completely filled without any voids in the mixture 200. Topping off of the mold tool with additional mixture 200 would then eliminate any such voids.

Once the mold tool 300 has been finally sealed with the plug 450 consolidating of the mixture 200 may take place by application of a Cold Isostatic Press (CIP). In the embodiment shown, the mold tool 300 is made up of rubber or other CIP compatible material. With the mold tool 300 sealed with the plug 450 it may be placed in a CIP chamber 400. The CIP chamber 400 is filled with water or other CIP compatible medium and activated. The CIP chamber 400 may be activated by conventional means to compact the mixture 200 within the mold tool 300. In one embodiment the mold tool 300 is subjected to between about 25 and about 50 ksi of pressure in the CIP chamber 400. However, pressures outside of this range may be employed. Additionally, alternative techniques of physically stabilizing the mixture 200 of FIG. 2 may be employed altogether. For example, conventional die compaction, powder extrusion, or metal injection molding techniques may also be employed.

In an alternate embodiment in which powder injection molding (PIM) is employed, a conventional water, acetone, or alcohol soluble binder may be mixed with the metal 125 ahead of time. In this embodiment pore formers 250 may subsequently be mixed in to form the mixture 200 with conventional PIM processing to follow for solidification.

Once the mixture 200 of FIG. 2 has been consolidated into a solid form, it may be removed from the mold tool 300 for further processing as a green article 500. In the embodiment shown, the mixture 200 has actually been compacted into an overlay metal 520 (as described above). The overlay metal 520 is now mechanically coupled to a underlying metal 350 forming a single green article 500 as shown in FIG. 5.

Figure 5:
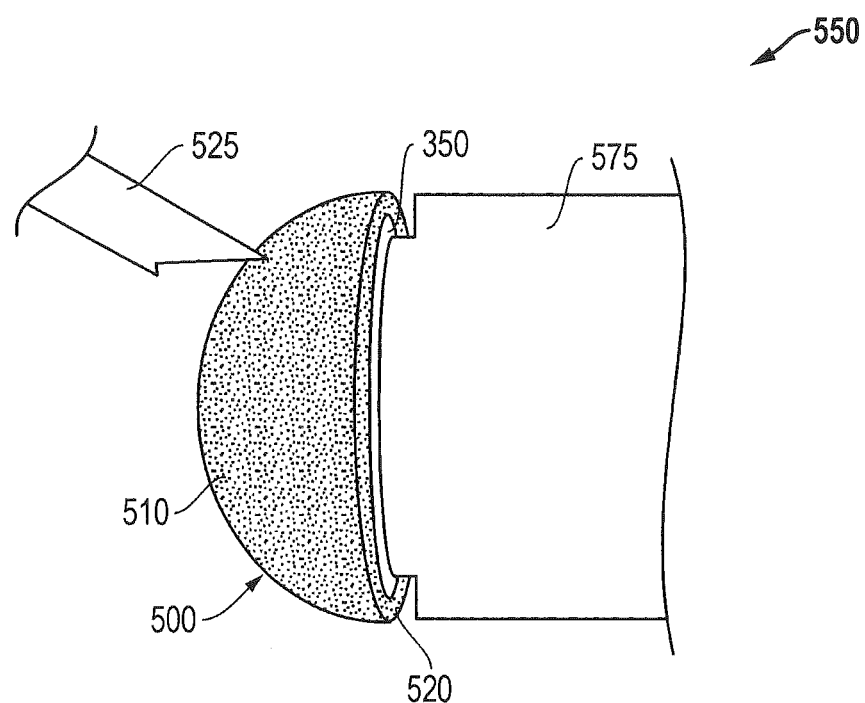
FIG. 5 is a side perspective view of an embodiment of a green article of the mixture of FIG. 2 recovered from the mold tool of FIG. 4 and shaped by a lathe.

With reference to the embodiment of FIG. 5 and added reference to FIG. 2, the overlay metal 520 of the green article 500 is configured to display uniformly porous character whereas the underlying metal 350 is configured to display negligible, if any, porosity. Therefore, the green article 500 on the whole is conditioned to provide a tailored gradient of pore character therethrough. Nevertheless, having been consolidated by CIP alone in the embodiment shown, the green article 500 still lacks the strength of a sintered metal. Furthermore, pore formers 250 remain in the overlay metal 520 and additional shaping of the green article 500 may be desired. Therefore, additional processing of the green article 500 may be undertaken as described below.

Continuing with reference to FIGS. 2 and 5, the green article 500 may optionally be pre-sintered to increase its tensile strength before removing the pore formers 250. That is, as described below, it may be desirable to leave the pore formers 250 within the green article 500 during any machining to help preserve pore integrity. In the embodiments shown, the green article 500 may be sintered at between about 500° C. and about 1,000° C. for an hour or more in the presence of an inert gas such as argon. In this manner sinter bonds may be formed within the green article 500 adding to the strength of the compact. In one embodiment, the homogenizing agent 255 may be dried from the green article 500 at this time if this has not already taken place.

The above described presintering may take place at a temperature high enough to promote development of sinter bonds but at a low enough temperature to allow further sintering to take place during later processing. In this manner the trapping of pore formers 250 in the green article 500 is avoided. In light of this concern, the particular parameters of the presintering are largely dependant on the metal 125 involved. For example, in an embodiment where titanium powder is provided as the metal 125, a temperature of 880° C. will not be exceeded during the presintering.

As referenced above, the green article 500 with increased strength and remaining pore formers 250, protecting the integrity of pores, may then be subjected to mechanical shaping or green machining. With additional reference to FIG. 6, in one embodiment, the green article 500, and ultimately the porous metal article 600 may be configured to display a roughened surface, or particular texture thereat. For example, the green article 500 may be shaped in this fashion to provide ingrowth surfaces where the porous metal article 600 is to be employed as a biological implant.

Continuing with reference to FIGS. 2, 5, and 6, mechanically shaping the green article 500 may take place before removal of pore formers 250 and in advance of final sintering as noted above. In this manner, pores at the surface of the green article 500 are maintained in a relatively open state by the pore formers 250 themselves during the machining. This helps avoid the undesired effect of physically isolating the porosity of the porous metal article 600.

In the embodiment shown, the green article 500 is shaped at a lathe 550 by the positioning thereof on a lathe support 575. In one embodiment the green article 500 is vacuum secured to the lathe support 575 minimizing contact therewith. The underlying metal 350 is coupled to the lathe support 575 exposing the overlay metal 520 for shaping by a shaping implement 525. In the embodiment shown, the surface of the overlay metal 520 is affected by the shaping implement 525 such that the outer diameter of the green article 500 is reduced to a degree. Nevertheless, as indicated above, the presence of pore former 250 in the pores of the overlay metal 520 protects pore integrity as the shaping implement 525 shapes the surface of the green article 500.

Once the green article 500 has been mechanically shaped and finished it may be removed from the lathe 550 and submerged in an extraction fluid for removal of pore formers 250 therefrom. In the embodiments described herein, materials are used in forming the green 500 and porous metal 600 articles that lend themselves to a water-based extraction. Use of a water-based extraction helps eliminate environmental, health and safety concerns. Nevertheless, other techniques may be employed. For example, other fluids, including gasses and liquids may be used depending on the dissolution properties of the extractable pore-former 250. However, as described herein, the pore formers 250 may be materials such as a metal salt. The ionic nature of the salt renders it susceptible to extraction by placing the green article 500 in a water bath. That is, the metal salt is soluble in water.

In order to confirm dissolution of the pore formers 250 into the extraction fluid, conventional monitoring and analysis of the extraction fluid may take place during the extraction. For example, where water is employed as the extraction fluid, the amount of extractable material in the water can be measured in ppm by a conductivity meter. Alternatively, reduction of the weight of the transforming green article 500 may be monitored over the course of the extraction.

As described above, and with continued reference to FIGS. 2, 5, and 6, the pore formers 250 have been removed from the green article 500 to provide a porous metal article 600. The extraction of the pore formers 250 leaves pores in the porous metal article 600 which retain the dimensional properties of the pore formers 250 used to form them. This has been achieved in a manner, water-based extraction, that leaves the chemical and mechanical integrity of the articles (500, 600) substantially unaffected. That is, rather than employing high temperature vaporization, highly reactive solvents or other more severe measures that might alter the character of the final porous metal article 600, the pore formers 250 have been removed by the mere introduction of water. This is made possible by the particular combination of metal 125 and pore formers 250 selected. For example, in an embodiment where titanium metal 125 and potassium chloride pore former 250 are employed, the pore former 250 may be removed from the green article 500 by water extraction. This is achieved without damage to the integrity of the metal matrix left behind by either the water involved or the presence of vaporized pore former 250 (i.e. as vaporization has not been utilized).

Continuing with reference to FIGS. 2, 5, and 6, once extraction of the pore formers 250 is completed, final sintering of the now porous metal article 600 may proceed to provide added mechanical or tensile strength thereto. This is achieved by way of heating the porous metal article 600 to provide sinter bonds throughout. In one embodiment, removal of the homogenizing agent 255 is also accomplished at this time. Additionally, the final porous metal article 600 may also be subjected to post sintering processes such as hot isostatic pressing (HIP) or other applications to provide added density.

The sintering conditions are determined by the properties of the porous metal article 600 that is being sintered. Times, temperatures, pressures and atmospheres used in a sintering cycle are selected based on the nature of the material being sintered. In embodiments described herein the porous metal article 600 may be placed in a sintering furnace and heated from room temperature at a rate of between about 5° C. to about 15° C. per minute. Heating of the porous metal article 600 in this manner may proceed up to between about 1000° C. and about 1500° C., preferably between about 1150° C. and about 1400° C. Sintering may continue for a period of between about 30 minutes and about 4 hours under partial pressure of an inert gas such as argon. The sintered porous metal article 600 may then be removed from the sintering furnace and cooled leaving it of increased strength and durability. For example, the porous metal article 600 may display tensile and shear bond strengths exceeding about 25-50 megapascals (MPa). As described below, the sintered metal article 600 may then be employed in a variety of applications such as for use as a biological implant.

While the described process of sintering increases the strength of the porous metal article 600 it also reduces its size proportionally. As such, the pore formers 250 as well as the green article 500 are accordingly configured in an oversized fashion as alluded to earlier. The overall shrinkage of the porous metal article 600 will be dependant the degree of densification provided thereto by the sintering. This will be determined by factors such as the dimensions and density of the metal 125 and the original mixture 200 as well as its chemistry and the carbon loss or oxygen pick-up during processing. However, as a practical matter, embodiments described herein include very consistent and repeatable techniques. Therefore, once shrinkage is determined for any particularly configured and processed porous metal article 600, the pore-formers 250 and green articles 500 may be sized and configured accordingly to account for the shrinkage. Thus, precise control over the pore character and sizing of the porous metal article 600 itself may be exercised.

The above-described sintering takes place after the extraction of the pore formers 250 as noted. This reduces the risk of the sintering leading to contamination of the porous metal article with the pore-formers 250. Thus, in embodiments described herein, neither vaporization, sintering, or any other potentially volatile application is employed in such a manner as to risk contamination of the porous metal article 600 with material of the pore formers 250.

Referring now to FIG. 6, a porous metal article 600 has been formed as described above. In the embodiment shown, the porous metal article 600 is to be used as a biological implant in the form of an acetabular shell or cup for a hip joint 610. The article 600 may be provided with a biological coating and implanted into a socket 650 at a pelvis 625 to receive and secure the head 675 of a femur 680.

As shown, the porous metal article 600 includes a porous portion (i.e. of overlay metal 520) and a non-porous portion (i.e. the underlying metal 350). As such, the porous metal article 600 as a whole may be considered to be of a particular tailored porosity. That is, from a portion exhibiting porosity to a portion exhibiting none. Further, the porosity of the porous portion of overlay metal 520 is precisely configured and of a uniform pore distribution as provided through techniques described above. As such, bone at the socket 650 of the pelvis 625 is provided with a uniquely homogeneous porous matrix substrate within which to integrate. By the same token, the head 675 of the femur may be secured by the concave and smooth non-porous underlying metal 350 of the porous metal article 600. Thus, embodiments described herein may be employed to provide a single co-formed porous metal article 600 displaying the character to provide both physical security via a porous matrix (overlay metal 520) as well as flexibility via a smooth non-porous portion (underlying metal 350) of the same material as the matrix.

Figure 7:
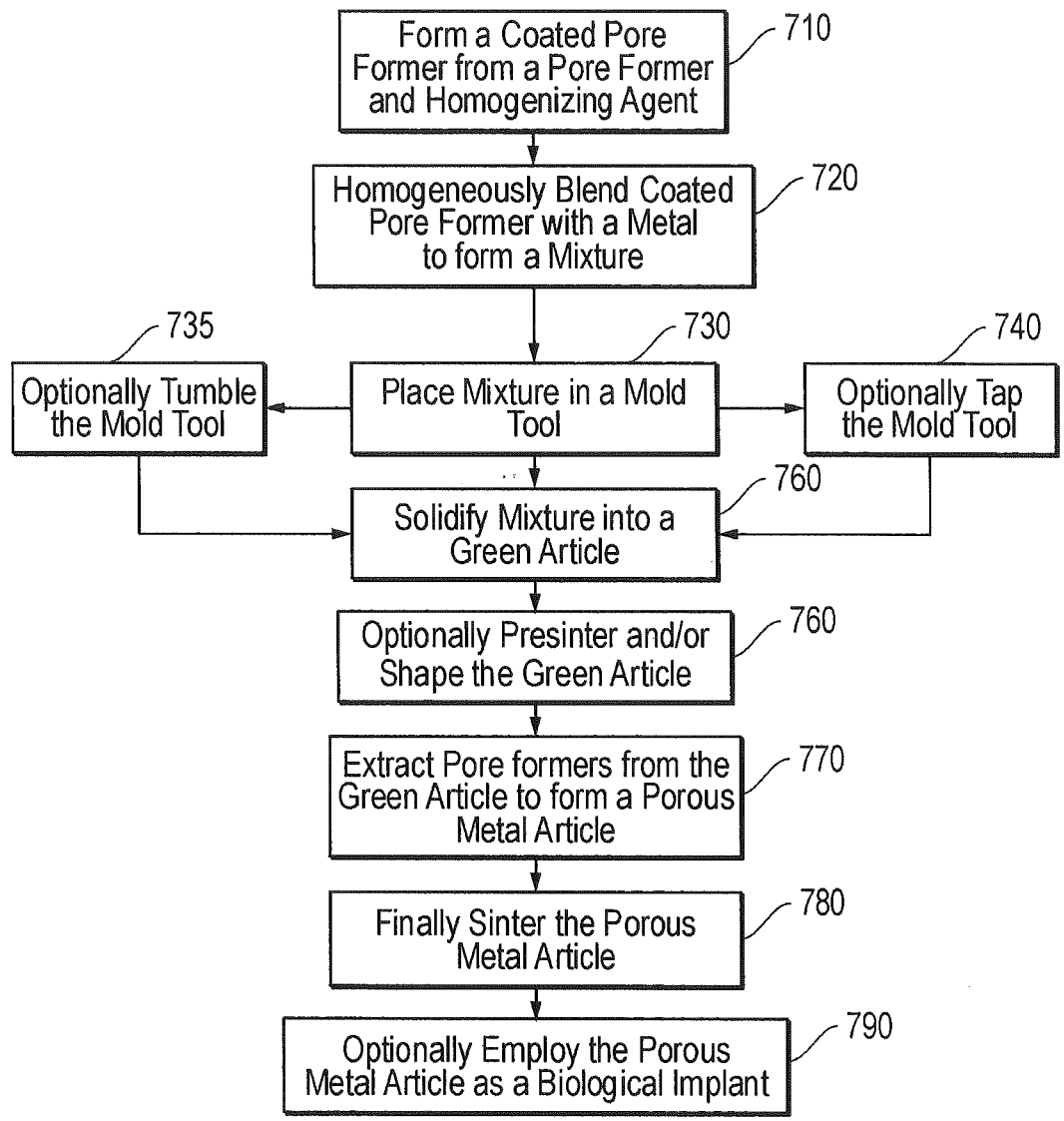
FIG. 7 is a flow chart describing an embodiment of forming a porous metal article of tailored porosity for use as a biological implant.

With particular reference to the flow-chart of FIG. 7, in addition FIGS. 1-6 described above, an embodiment of forming a porous metal article 600 of controlled porosity and for use as a biological implant is summarized. As noted at 710 a pore former 250 and homogenizing agent 255 are combined to create a coated pore former 100. A metal 125 is blended with the coated pore former 250 to form a homogeneous mixture 200 thereof as indicated at 720. The homogeneous nature of the mixture 200 is maintained by properties of the homogenizing agent 255.

The above described mixture 200 is placed in a mold tool 300 as indicated at 730. The mold tool 300 may be optionally tumbled and tapped (735, 740) before the mixture 200 therein is solidified into a green article 500 as indicated at 750. As noted at 760, the solid green article 500 may be presintered and/or shaped before pore formers 250 therein are extracted to form a porous metal article 600 (see 770). Extraction 770 takes place in a manner that preserves and ensures the integrity of the formed porous metal article 600. In the embodiment shown, the porous metal article 600 may then be finally sintered and employed as a biological implant as indicated at 780 and 790.

Embodiments of a biological implant may be of a particularly configured interconnecting porosity through techniques described above. For example, to support bone ingrowth into the porous portion of an article, an interconnecting pore ratio of between about 2:1 and about 5:1 of major pore size to minor pore size may be employed. That is, in an open cell embodiment, any given pore former size employed will result in a porous portion displaying pores relative to the size of the pore former (i.e. major pore size) and porosity relative to the overlap or interconnectivity of the pores (i.e. minor pore size). The porosity of the porous portion in such an embodiment may be between about 60% and about 85%.

In a preferred embodiment, an interconnecting pore ratio may be between about 2.5:1 and about 4.5:1. Such ratios may be particularly advantageous to enhancing bone ingrowth into a porous portion of a biological implant. In one embodiment, a porosity of about 70% is provided to the porous portion of the article via pore formers of about 1,000 microns in diameter. This may result in a minor pore size of about 270 microns and thus, an interconnecting pore ratio of about 3.7:1. In another embodiment, a porosity of about 70% is provided to the porous portion of the article via pore formers of about 575 microns in diameter. This may result in a minor pore size of about 160 microns and thus, an interconnecting pore ratio of about 3.6:1. Regardless, the interconnecting pore ratio will be substantially uniform throughout the porous portion of the article.

The embodiments described herein provide techniques of employing solid pore formers to create a porous metal article in a manner that allows for a controlled pore character to be displayed by the article with respect to pore size, morphology and uniformity of distribution. Certain embodiments may even provide for a tailored pore character to extend throughout the article such that one portion of the article is configured of one pore character and level of porosity and another portion of a second pore character or level of porosity. Furthermore, porous metal articles may be formed as described in a manner that removes solid pore formers without otherwise altering the ultimate physical or chemical character of the porous metal article itself.

Although exemplary embodiments describe the forming of particular porous metal articles in the form of layered biological implants, additional embodiments are possible. For example, filters, flow control devices, and closed cell porous articles may be formed employing techniques described herein. Furthermore, many changes, modifications, and substitutions may be made without departing from the spirit and scope of the described embodiments.

The invention claimed is:

1. A porous article comprising a porous portion with an average ratio between about 2:1 and about 5:1 of major pore size to minor pore size, having a substantially uniform pore distribution and a porosity of at least 70 percent, the porous article for use as a biological implant.

2. The porous article of claim 1 wherein the porous portion is a first portion to support bone ingrowth, the porous article having a second portion of negligible porosity to avoid bone ingrowth.

3. The porous article of claim 1 wherein the biological implant is an acetabular cup.

* * * * *